United States Patent [19]
Gauthier-Lafaye et al.

[11] Patent Number: 4,511,517
[45] Date of Patent: Apr. 16, 1985

[54] CARBONYLATION OF METHYL ACETATE

[75] Inventors: Jean Gauthier-Lafaye, Lyons; Robert Perron, Charly; Claude Doussain, Saint-Fons, all of France

[73] Assignee: Rhone-Poulenc Chimie de Base, Courbevoie, France

[21] Appl. No.: 398,802

[22] Filed: Jul. 16, 1982

[30] Foreign Application Priority Data

Jul. 17, 1981 [FR] France .................. 81 14123

[51] Int. Cl.$^3$ ............................................. C07C 51/56
[52] U.S. Cl. .................................................... 260/549
[58] Field of Search ............... 260/549; 560/232; 568/484; 562/517

[56] References Cited
U.S. PATENT DOCUMENTS

| | | | |
|---|---|---|---|
| 2,593,440 | 4/1952 | Hagemeyer | 260/549 |
| 2,730,546 | 1/1956 | Reppe et al. | 260/549 |
| 2,789,137 | 4/1957 | Reppe et al. | 260/546 |
| 2,805,248 | 9/1957 | Friederich et al. | 260/546 |
| 3,989,751 | 11/1976 | Forster et al. | 260/546 |

Primary Examiner—Natalie Trousof
Assistant Examiner—L. Hendriksen
Attorney, Agent, or Firm—Burns, Doane, Swecker & Mathis

[57] ABSTRACT

Methyl acetate is carbonylated, advantageously to acetic anhydride, in a homogeneous liquid phase, advantageously in a virtually anhydrous reaction medium, in the presence of (a) a cobalt source, (b) a source of iron in the zero oxidation state, (c) an ionic iodide of the formula $A^+I^-$ in which $A^+$ is a nitrogen group quaternary onium cation, or an alkali metal cation, and, (d) if appropriate, a carboxylate of the formula $A'^{n+}(OCOR)_n^-$, in which n is 1 or 2 and $A'^{n+}$ is defined as was $A^+$, or is an alkaline earth metal cation, with $A'^{n+}$ and $A^+$ either being the same or different, and R is an alkyl, aralkyl or aryl radical having a maximum of 8 carbon atoms, with the total amount of halogen compounds present in the carbonylation reaction medium (expressed in gram atoms of halogen and designated by $X_T$) being such that the atomic ratio $X_T/(A^+ + n.A'^{n+})$ is less than or equal to 1.

20 Claims, No Drawings

CARBONYLATION OF METHYL ACETATE

CROSS-REFERENCE TO RELATED APPLICATIONS

Gauthier-Lafaye et al copending application, Ser. No. 387,467, filed June 11, 1982, and Gauthier-Lafaye et al copending application, Ser. No. 398,806, filed concurrently herewith, both assigned to the assignee hereof.

BACKGROUND OF THE INVENTION

1. Field of the Invention

The present invention relates to the carbonylation of methyl acetate, advantageously in a virtually anhydrous medium, and, more especially, relates to the carbonylation of methyl acetate, advantageously in a virtually anhydrous medium, in the presence of a cobalt-based catalyst.

2. Description of the Prior Art

U.S. Pat. No. 2,730,546 describes the carbonylation of methyl acetate to prepare acetic anhydride, in the presence of a catalyst selected from among the cobalt complexes of the general formula:

$$[R_4A]_2CoX_4$$

in which X represents a bromine or iodine atom, A represents a nitrogen or phosphorous atom and R represents a lower alkyl radical, for example.

These complexes can be formed in situ by introduction into suitable reaction vessel of, firstly, a cobalt halide (CoX'$_2$) and secondly a quaternary ammonium (or phosphonium) halide (R$_4$AX). The formation of the subject complexes can thus be represented by the following reaction:

$$2(R_4AX) + CoX'_2 \rightarrow [R_4A]_2CoX'_2X_2.$$

However, the efficacy of these cobalt-based catalysts appeared to be relatively low. This type of process, the value of which is not contested in principle, has to date proven unacceptable on an industrial scale.

French Pat. No. 2,242,362 (corresponding to U.S. priority application, Ser. No. 394,220 and Ser. No. 467,997, respectively filed on Sept. 4, 1973 and May 8, 1974 the latter having issued as U.S. Pat. No. 3,904,134) describes a two-stage process for the preparation of acetic anhydride, in which, in a first step, methyl bromide or, preferably, methyl iodide is carbonylated to provide the corresponding acetyl halide, such acetyl halide in turn being reacted with methyl acetate, in a second step, to provide acetic anhydride, which corresponds to the following reaction scheme, in the event that methyl iodide is the starting material:

Step 1:

$$CH_3I + CO \rightarrow CH_3COI$$

Step 2:

$$CH_3COI + CH_3COOCH_3 \rightarrow (CH_3CO)_2O + CH_3I.$$

As is readily apparent from this scheme, the methyl iodide, which is the starting material of step 1, is "regenerated" in step 2. Step 1 is advantageously carried out in the presence of a rhodium-based catalyst; step 2 would be assisted by the presence of lithium and/or chromium. Both steps would be assisted by the presence of lithium and/or chromium. Both steps can be carried out in one and the same reaction zone, which will then contain methyl iodide, methyl acetate, rhodium and, if appropriate, lithium and/or chromium, and even acetyl iodide, into which zone carbon monoxide will also be introduced.

U.S. Pat. No. 4,115,444 proposes an improvement to the technique described in the abovementioned French patent, which improvement consists in adding, to the reaction medium, an organic phosphorus or nitrogen compound in which the phosphorus or the nitrogen is trivalent, and confirms the potential value, in this reaction, of catalyst systems based on rhodium, or even palladium or iridium, and chromium.

French Pat. No. 2,303,788 (corresponding to U.S. priority application Ser. No. 556,749 and Ser. No. 654,662, respectively filed on Mar. 10, 1975 and Feb. 5, 1976) reflects that the presence of a large amount of hydrogen in the reaction medium above described has a considerable influence upon the direction of the reaction. In fact, under these conditions, a mixture is obtained which contains a preponderant proportion of acetic acid and variable amounts of ethylidene diacetate, acetic anhydride and acetaldehyde.

The principal value of these processes employing catalysts based on rhodium, or even palladium or iridium, the systems based on the pair (rhodium/chromium) appearing to be the most active, essentially resides in the possibility which they present of obtaining acetic anhydride starting from methyl acetate, utilizing carbon monoxide partial pressures which are lower than those required in the earlier processes.

Nevertheless, the attempts to develop this type of process, even on a simple pilot plant scale, have encountered serious difficulties.

A first series of difficulties arises from the fact that the catalysts based on rhodium or palladium, or even iridium, which metals are extremely rare and expensive, are deactivated, in particular during the treatments required to recover the reaction product (or products). Because of the cost of these catalysts, it is essential to regenerate same. Furthermore, the conditions required to convert these metal compounds to catalytically active species in the carbonylation reaction are most frequently incompatible with those required to maintain the chromium-based co-catalysts in their active form in this same reaction. Still further, the losses of rhodium, for example, which seem to be unavoidable at the various points in an industrial plant, severely impair the economics of such a process.

A second series of difficulties is derived from the presence, required for the reaction to proceed well and for the stabilization of the rhodium, of large amounts of methyl (or acetyl) iodide, which involves significant risks of corrosion at the various points in an industrial installation. Furthermore, the methyl iodide and/or certain of its derivatives formed in the reaction medium are responsible for an unacceptable contamination of the reaction product (or products), which makes it necessary to carry out additional steps in order to remove the iodides whose presence in the reaction products proves to be undesirable. For obvious economic reasons, these iodine derivatives, which are present in large amounts not only in the products but also in various effluents originating from the reaction zone, must be recovered, and this involves additional treatment stages.

The various problems associated with this type of process, which are difficult to solve, will become more clearly apparent from French Pat. Nos. 2,438,023 and 2,438,024 (corresponding respectively to U.S. priority application, Ser. No. 949,344 and Ser. No. 949,345, filed Oct. 6, 1978, these applications having issued as U.S. Pat. Nos. 4,252,741 and 4,246,195, respectively) and U.S. Pat. No. 4,241,219.

Too, it is also well known that methyl acetate can be obtained by reacting acetic acid with methanol, it being possible for the acetic acid to be produced by the carbonylation of methanol and for the methanol in turn to be prepared by the hydrogenation of carbon monoxide. The reactions in question can be represented as follows:

$$CO + 2H_2 \rightarrow CH_3OH \quad (a)$$

$$CH_3OH + CO \rightarrow CH_3COOH \quad (b)$$

$$CH_3COOH + CH_3OH \rightarrow CH_3COOCH_3 + H_2O \quad (c)$$

The carbonylation of methyl acetate in a substantially anhydrous medium makes it possible to obtain acetic anhydride according to the following reaction:

$$CH_3COOCH_3 + CO \rightarrow CH_3CO-O-COCH_3 \quad (1)$$

Thus, the value of a process for the carbonylation of methyl acetate to yield acetic anhydride (1) is clearly apparent if reactions (a) to (c) above are also considered, since, overall, this sequence amounts to a process by which acetic anhydride is produced beginning from carbon monoxide and hydrogen.

Furthermore, cobalt being a common metal, its use in a process for the carbonylation of methyl acetate would be desirable. Nonetheless, to date the prior art has almost exclusively focused upon the rhodium based catalyst systems in such process.

SUMMARY OF THE INVENTION

Accordingly, a major object of the present invention is the provision of an improved process to carbonylate methyl acetate effectively, advantageously in a virtually anhydrous medium, in the presence of a cobalt-based catalyst system.

Briefly, the present invention features a process for the carbonylation of methyl acetate in a homogeneous liquid phase, advantageously in an essentially anhydrous medium, in the presence of:

(a) a source of cobalt;
(b) a source of iron in the zero oxidation state;
(c) an ionic iodide of the formula:

$$A^+I^-$$

in which $A^+$ is a cation selected from the group comprising the quaternary onium cations derived from the elements of the nitrogen group, and the alkali metal cations; and (d) if appropriate, a carboxylate of the formula:

$$A'^{n+}(OCOR)_n^-$$

in which n is equal to 1 or 2, and $A'^{n+}$ has the meaning given above for $A^+$, with $A'^{n+}$ and $A^+$ being the same or different, and further wherein $A'^{n+}$ may also be an alkaline earth metal cation, and R is an alkyl, aralkyl or aryl radical having a maximum of 8 carbon atoms; with the total amount of halogen compounds present in the reaction medium (expressed in gram atoms of halogen and designated as $X_T$ hereinafter) being such that the atomic ratio $X_T/(A^+ + n.A'^{n+})$ is less than or equal to 1.

DETAILED DESCRIPTION OF THE INVENTION

More particularly according to this invention, the subject carbonylation of methyl acetate is indeed quite notable in several respects. In fact, it has been found, totally unexpectedly, that the addition of a source of iron in zero oxidation state to the reaction medium containing ingredients of the type (a), the type (c) and, if appropriate, the type (d) set forth above, makes it possible to prepare acetic anhydride, in particular, with an especially high hourly productivity, whereas, under the same reaction conditions, cobalt by itself possesses but mediocre carbonylating activity and efficacy in the reaction envisaged, and iron by itself, under these same conditions, provides virtually no carbonylating activity whatsoever.

Without wishing to be bound to any particular theory or reaction mechanism, it would appear that the carbonylating activity must be attributed, in the present process, to the source of cobalt, which, under the reaction conditions, would be converted to a catalytically active species, the precise nature of which has not as yet been totally elucidated.

The second metal constituent of the subject catalyst system (the source of iron in the zero oxidation state), which itself possesses virtually no carbonylating activity, apparently serves only to increase the activity and/or the concentration of active cobalt species or its useful life, if appropriate. The reasons for this noteworthy influence is unknown, but could lie in a change in the oxidation state and/or the arrangement, or even in the nature, of the ligands of the central cobalt atom. Stated differently, the source of iron in zero oxidation state would serve to facilitate the production of the active form of cobalt in the reaction medium.

Furthermore, it too has been found, also totally surprisingly, that, in contrast to the direction of the prior art, the efficacy of the present process is not related to the presence of large amounts of methyl iodide. On the contrary, when methyl iodide is added upon carrying out the process of the invention, a considerable reduction in process efficacy is observed.

The precise reason for the adverse influence of methyl iodide, a phenomenon which is in total contradistinction to the teachings of the prior art, is unknown. Also without wishing to be bound to any particular theory or explanation, it is assumed that the methyl iodide, when it is present in considerable amounts, disturbs or disrupts the complex equilibria which would, in particular, cause the very high reactivity of the cobalt under the conditions described.

On the other hand, the carbonylating activity of the catalyst system above described is not related to the precise nature of the cobalt compound or compounds initially introduced. It is possible, within the scope of the present invention, to use any source of cobalt whatsoever which is capable of reacting with carbon monoxide in the reaction medium to provide cobalt carbonyl complexes. Examples of the typical sources of cobalt are finely divided cobalt metal, inorganic cobalt salts (nitrate, carbonate, halides, and the like) or organic salts, in particular the carboxylates. It is also possible to employ cobalt carbonyls or hydrocarbonyls. Among the cobalt derivatives which are suitable for carrying out the process according to the invention, representative are the formate, the acetate and, more particularly, dicobalt octacarbonyl.

The precise amount of cobalt employed in the reaction medium is not of fundamental importance. In general, the reaction is carried out with an amount of cobalt which is such that the concentration in the reaction medium, expressed in milligram atoms per liter (mg atoms/l), ranges from 0.1 to 500 and preferably ranges from 0.5 to 100 mg atoms/l.

One advantage of the present process is the fact that it is possible to obtain good results with a low cobalt concentration.

A source of iron in the zero oxidation state is also employed to carry out the subject process. Such source of iron in the zero oxidation state is advantageously iron metal, iron pentacarbonyl, or an alloy containing various metals, the iron content of which being at least 20% (by weight). Stainless steels, in particular the steel Z8 CNDT 17-12 (Afnor Standard Specification), and iron chromium alloys are exemplary of alloys which are suitable for effecting the subject process.

Iron metal or its alloys can be used in any convenient form. Thus, it is possible to use powders, filings, optionally braided wires, solid blocks, cylinders or plugs.

Furthermore, although the walls of the autoclave (or of the reactor), in the case where the latter has been made of stainless steel, for example, can make a considerable contribution to the conduct of the process of the invention, this contribution is nevertheless insufficient, and it is required in this case to also employ another source of iron in the zero oxidation state.

The amount of iron to be used is generally such that the atomic ratio Fe/Co is greater than or equal to 1 and preferably greater than or equal to 5. To carry out the present process satisfactorily, the atomic ratio Fe/Co will be greater than or equal to 10. It is not necessary for this ratio to exceed 1,000.

The process according to the present invention also requires the presence of an ionic iodide of the formula:

$$A^+I^-$$

in which $A^+$ is a cation selected from the group comprising the quaternary onium cations derived from the elements of the nitrogen group of the Periodic Table, and the alkali metal cations.

By the expression "quaternary onium cations derived from elements of the nitrogen group" there are intended cations formed from nitrogen, phosphorus, arsenic or antimony and from four identical or different, monovalent hydrocarbon groups, the free valency of which being borne by a carbon atom, each such group being bonded to the above-mentioned element via said free valency, and it is furthermore possible for any two such groups to together from a single divalent radical.

Among these compounds, preferred are the quaternary phosphonium (or ammonium) iodides. The cations of these iodides are conveniently represented by the formulae (I) to (III) below:

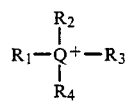
(I)

in which Q represents a nitrogen or phosphorous atom and $R_1$, $R_2$, $R_3$ and $R_4$, which can be identical or different, represent organic radicals, the free valency of which being borne by a carbon atom, it being possible, if appropriate, for any two of these various radicals to together form a single divalent radical.

More specifically, $R_1$, $R_2$, $R_3$ and $R_4$ are preferably linear or branched chain alkyl radicals, monocyclic cycloalkyl radicals, aralkyl (for example, benzyl) radicals or aryl radicals, having at most 16 carbon atoms and can, if appropriate, be substituted by 1 to 3 alkyl radicals having from 1 to 4 carbon atoms, it being possible, if appropriate, for two of the radicals $R_1$ to $R_4$ to together form a single divalent alkylene or alkenylene radical containing 3 to 6 carbon atoms (for example, a tetramethylene or hexamethylene radical) and, if appropriate, comprising 1 or 2 ethylenic double bonds, and it also being possible for said radical to be substituted with from 1 to 3 alkyl substituents having from 1 to 4 carbon atoms.

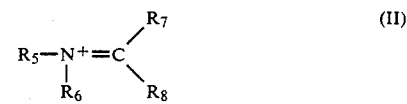

in which $R_5$, $R_6$, $R_7$ and $R_8$, which are identical or different, represent alkyl radicals having from 1 to 4 carbon atoms, it also being possible for one of the radicals $R_7$ or $R_8$ to represent hydrogen, and it being possible, if appropriate, for $R_7$ and $R_8$ to together form a single divalent alkylene radical containing from 3 to 6 carbon atoms, for example, a tetramethylene or hexamethylene radical; $R_6$ and $R_7$ or $R_8$ can together form a single divalent alkylene or alkenylene radical containing 4 carbon atoms and, if appropriate, comprise 1 or 2 ethylenic double bonds, the nitrogen atom then being included in a heterocyclic ring to form, for example, a pyridinium cation.

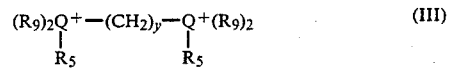

in which $R_5$ and $Q^+$ are as defined above, $R_9$, which can be identical to $R_5$, represents an alkyl radical having from 1 to 4 carbon atoms or a phenyl radical, and $y$ is an integer ranging from 1 to 10 inclusive and preferably from 1 to 6 inclusive. The following are specific examples of quaternary ammonium iodides which are suitable for carrying out the present process: tetramethylammonium, triethylmethylammonium tributylmethylammonium, trimethyl-(n-propyl)-ammonium, tetraethylammonium, tetrabutylammonium, dodecyltrimethylammonium, benzyltrimethyl-ammonium, benzyldimethylpropylammonium, benzyldimethyloctylammonium, dimethyldiphenylammonium, methyltriphenylammonium, N,N-dimethyl-trimethyleneammonium, N,N-diethyl-trimethyleneammonium, N,N-dimethyl-tetramethyleneammonium, N,N-diethyl-tetramethyleneammonium, N-methylpyridinium, N-ethylpyridinium and N-methylpicolinium iodides.

The following are specific examples of quaternary phosphonium iodides which are also suitable for carrying out the present process: tetramethylphosphonium, ethyltrimethylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri-(isopropyl)phosphonium, methyl-tri-(n-propyl)-phosphonium, methyl-tri-(n-butyl)-phosphonium, methyl-tri-(2-methylpropyl)-phosphonium, methyltricyclohexylphosphonium, methyltriphenylphosphonium, methyltribenzylphosphonium, methyl-tri-(4-methylphenyl)-phosphonium, methyltrixylylphosphonium, diethylmethylphenylphosphonium, dibenzylmethylphenylphosphonium, ethyltriphenylphosphonium, tetraethylphosphonium ethyl-tri-(n-propyl)-phosphonium, triethylpentylphosphonium, ethyltriphenylphosphonium, n-butyl-tri-(n-propyl)-phosphonium, butyltriphenylphosphonium, benzyltriphenylphosphonium, ($\beta$-phenylethyl)-dimethylphenylphosphonium, tetraphenylphosphonium and triphenyl-(4-methylphenyl)-phosphonium iodides.

The precise nature of the quaternary ammonium or phosphonium cation is not of critical importance within the scope of the present invention. The selection from among such compounds is governed more by considerations of a practical nature, such as the solubility in the reaction medium, the availability and the convenience of use.

In this respect, the quaternary or phosphonium iodides represented either by the formula (I) in which any one of the radicals $R_1$ to $R_4$ is selected from among linear alkyl radicals having from 1 to 4 carbon atoms, or by the formula (II) or (III) in which $R_5$ (or $R_6$) is also an alkyl radical having from 1 to 4 carbon atoms, are particularly suitable.

Moreover the preferred ammonium iodides are those of which the cations correspond to the formula (I) in which all the radicals $R_1$ to $R_4$ are selected from among linear alkyl radicals having from 1 to 4 carbon atoms, and in which at least three of same are identical.

Likewise, the preferred quaternary phosphonium iodides are those of which the cations correspond to the formula (I) in which any one of the radicals $R_1$ to $R_4$ represents a linear alkyl radical having from 1 to 4 carbon atoms, the other three radicals being identical and being selected from among phenyl, tolyl or xylyl radicals.

Alkali metal iodides are also suitable for carrying out the present invention. However, in the case where these iodides are indeed used, it is also appropriate to introduce, into the reaction medium, a solvent selected from among tetramethylenesulfone, tetramethylurea, N-methylpyrrolidone and monocarboxylic acid amines which are derived from monocarboxylic acids having at most 8 carbon atoms and in which the nitrogen atom contains two alkyl substituents having at most 4 carbon atoms. This type of solvent is used in an amount of 10 to 50% (by volume) of the reaction medium, although higher or lower proportions can also be used.

The amount of ionic iodide to be used within the scope of the present invention is generally such that the molar ratio $I^-/Co$ is greater than or equal to 5 and preferably greater than or equal to 10. No advantage is gained if this ratio exceeds a value of 200. The molar ratio $I^-/Co$ will advantageously be fixed at a value ranging from 15 to 100.

Also as above indicated, the present invention can also be carried out in the presence of a carboxylate of the formula:

in which n is equal to 1 or 2, $A'^{n+}$ has the meaning given above for $A^+$, it furthermore being possible for $A'^{n+}$ and $A^+$ to be identical or different, and also for $A'^{n+}$ to be an alkaline earth metal cation, and R is an alkyl, aralkyl or aryl radical having a maximum of 8 carbon atoms.

This carboxylate embodiment is quite advantageous within the scope of the present invention when using an alkali metal iodide. In fact, the carboxylates in question seem to limit the in situ production of methyl iodide (the adverse effect of which in the present process having already been pointed out), which can be formed by reaction of the said iodides with the methyl acetate (starting material) according to the equation given below for the particular case of lithium iodide, the formation of methyl iodide being greater when starting from lithium iodide than when starting from an equivalent amount of sodium iodide or potassium iodide (for example):

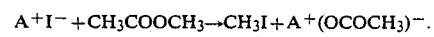

It is not necessary for the carboxylate $A'^{n+}(OCOR)_n^-$ to be derived from the same cation as the ionic iodide used. The carboxylate is advantageously an acetate.

It will be appreciated that certain acetates can be considered as the addition products of methyl acetate and a phosphine, an amine, an arsine or a stibine, according to the equation given for the particular case of triphenylphosphine for simplicity:

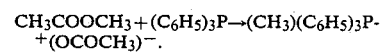

It is for this reason that each mol of phosphine, amine, arsine or stibine which may be introduced or fed will be considered as one gram equivalent of cation $A'^{n+}$ in the expression relating to the total amount of halogen ($X_T$) to that of the cations $A^+$ and $A'^{n+}$ present in the reaction medium.

If a carboxylate of the type defined above is used, the amount thereof is generally such that the molar ratio $A'^{n+}/A^+$ ranges from 0.01 to 20. Preferably, this ratio ranges from 0.05 to 10 and more advantageously from 0.1 to 5.

In one embodiment of the invention, which is especially advantageous in the event that the source of iron in the zero oxidation state is an alloy, the subject process is carried out in the presence of hydrogen. Within the scope of this embodiment, the hydrogen partial pressure, determined at 25° C., will then be at least 1 bar, preferably at least 3 bars, and even more preferably at least 10 bars. In general, the hydrogen partial pressure, measured at 25° C., will not exceed 100 bars; advantageously, it will be below 70 bars, and preferably below 50 bars.

Those skilled in this art will appreciate that the nature of the resultant product is a function of the proportion of water in the reaction medium. If the reaction is carried out in a reaction medium which contains the minimum possible amount of water (virtually anhydrous medium), taking account of the various applicable industrial constraints, acetic anhydride is selectively obtained. On the other hand, if the medium contains an appreciable amount of water, it is possible to obtain acetic acid in a proportion corresponding to that of the acetic anhydride obtained in a virtually anhydrous medium. Insofar as it proves economically more advantageous to produce acetic anhydride, the present process will advantageously be carried out in a virtually anhydrous medium.

Also as above indicated, it is necessary for the total amount of halogen compounds present in the reaction medium ($X_T$, expressed in gram atoms of halogen) to be such that the (atomic) ratio $X_T/(A^+ + n.A'^{n+})$ is less than or equal to 1.

This condition does not exclude the possibility of using halogens ($X_2$), halogen acids (HX), alkyl halides (RX) or cobalt halides ($CoX_2$), but implies that, if these types of compounds are introduced or fed in, it will be necessary to introduce or feed in either a carboxylate $[A'^{n+}(OCOR)_n^-]$ defined above, or a phosphine, an amine, an arsine or a stibine, in an amount which is at least equivalent to the number of gram atoms of halogen (X) introduced, if appropriate, by means of the above-mentioned halogen compounds. It is accepted that, under the reaction conditions, the halogen compounds $X_2$, HX and $CoX_2$ will react with the methyl acetate to produce a methyl halide, which in turn (together with the alkyl halides RX) will react with the phosphine, the amine, the arsine or the stibine to form the corresponding quaternary onium halide.

It is for this reason that, assuming that halogen compounds of the types $X_2$, HX, RX and $CoX_2$ are indeed used, each mol of phosphine, amine, arsine or stibine introduced in order to "neutralize", as it were, these sources of halogen will be considered as one gram equivalent of cation $A^+$ in the expression relating the total amount of halogen ($X_T$) to that of the cations $A^+$ and $A'^{n+}$ present in the reaction medium.

Furthermore, for the same reason as the alkyl halides, (RX), the methyl halide $CH_3X$ can react with the carboxylates $[A'^{n+}(OCOR)_n^-]$ to produce the corresponding ionic halides $(A'^{n+}X_n^-)$.

The phosphines, amines, arsines and stibines to be used, if appropriate, can be represented by the formula (IV) below:

(IV)

in which Q' represents a phosphorus, nitrogen, arsenic or antimony atom and $R_1$ to $R_3$ are as above defined.

It is advantageous to use a phosphine and more particularly triphenylphosphine.

According to a second embodiment of the present invention, which proves to be particularly advantageous in the case where the source of iron in the zero oxidation state is an alloy, and in the event that it is desirable to carry out the present process at a temperature which is above or equal to 160° C., or even above 180° C., the total pressure at this temperature being greater than or equal to 100 bars, the initial reaction medium contains, in addition to the methyl acetate and the various constituents of the subject catalyst system, a solvent selected from among aliphatic carboxylic acids having at most 8 carbon atoms. Among such acids, acetic acid is the preferred. For the process according to the invention to proceed satisfactorily, the carboxylic acid represents from 1 to 75% by volume of the reaction medium and preferably from 5 to 30% (by volume) of the said medium.

In this case, the initial reaction medium can also contain from 10 to 50% by volume of an additional solvent selected from the group comprising tetramethylenesulfone, tetramethylurea, N-methylpyrrolidone, monocarboxylic acid amides which are derived from acids having at most 8 carbon atoms and in which the nitrogen atom bears two alkyl substituents having at most 4 carbon atoms, and acetic anhydride.

The carbon monoxide partial pressure, measured at 25° C., is generally greater than 10 bars and preferably greater than 30 bars.

The reaction temperature, which can vary over wide limits, generally ranges from 60° to 300° C. The reaction is advantageously carried out at a temperature ranging from 80° to 240° C. and preferably at a temperature above 100° C., this being the range in which the catalyst system develops optimum efficacy.

One advantage of the present process is the possibility of carbonylating methyl acetate efficiently, even with a low concentration of cobalt, of iron in the zero oxidation state and of ionic iodide, under a total pressure, at the relevant temperature, on the order of 20 to 300 bars, which is therefore much smaller than that usually recommended for cobalt-based catalyst systems.

Another advantage of the present process is the disappearance of the various constraints associated with the use of the catalyst systems recently proposed for carrying out this carbonylation.

It too is known to the art that methyl acetate, which is the starting material in the present process, can be formed in situ from dimethyl ether; it is therefore also envisaged, within the scope of the present invention, to introduce or feed in dimethyl ether or a mixture of dimethyl ether and ethyl acetate.

Upon completion of the reaction, the products obtained can be easily separated, for example, by fractional distillation of the resulting mixture.

In order to further illustrate the present invention and the advantages thereof, the following specific examples are given, it being understood that same are intended only as illustrative and in nowise limitative.

In the Examples 1 to 33 and also in control experiments (a) to (f) to follow, the procedure employed was as follows:

Methyl acetate, one or more solvents, if appropriate, and the various constituents of the catalyst system were introduced into an autoclave having a capacity of 125 ml (fabricated of Hastelloy B2 in Examples 24 to 31 and of tantalum in all other examples, and in the control experiments.) After the autoclave had been closed, a carbon monoxide pressure and a hydrogen pressure, respectively designated by P(CO) and P(H$_2$) (values measured at 25° C.), were applied.

Shaking by means of a reciprocating system was commenced and the autoclave was then heated to the selected temperature, designated by T, over a period of time of about 25 minutes. The total pressure at this temperature, designated by P(T), was maintained substantially at the indicated value by successively introducing additional amounts of carbon monoxide containing a maximum of 1% (by volume) of hydrogen. After a reaction time designated by t, the autoclave was cooled and degassed. The reaction mixture was then analyzed by chromatography and potentiometry.

The following abbreviations are used in the examples:

| | |
|---|---|
| AcOMe: | denotes methyl acetate; |
| AcOH: | denotes acetic acid; |
| Ac₂O: | denotes acetic anhydride; |
| TMS: | denotes tetramethylenesulfone; |
| NMP: | denotes N—methylpyrrolidone; |
| TMU: | denotes tetramethylurea; |
| Pr: | denotes the productivity, expressed in grams of acetic anhydride per hour and per liter; |
| RY: | denotes the number of mols of acetic anhydride formed per 100 mols of methyl acetate introduced; |
| mg atom: | denotes milligram atom; |
| mmol: | denotes millimol |

All the pressures [P(CO), P(H$_2$) and (P$_T$)] are expressed in bars.

EXAMPLES 1 TO 12 CONTROL EXPERIMENTS (a) TO (c)

Table I below summarizes the particular reaction conditions and the results obtained in a series of experiments, which had the following conditions in common:

The reaction was carried out in the presence of 1 mg atom of cobalt, in the form of dicobalt octacarbonyl, namely, a concentration of 20 mg atom/l.

15 mmols of methyltriphenylphosphonium iodide (ionic iodide; I$^-$/Co=15) and iron powder were used, unless otherwise indicated.

T=210° C.; P(T)=250 bars; $X_T/(A^+ + n.A'^{n+})=1$,

In Example 8, an iron-chromium powder was used (18 mg atom of iron and 77 mg atom of chromium).

In Example 9, an iron-titanium powder was used (30 mg atom of iron and 30 mg atom of titanium); P(T)=150 bars.

Example 10 was carried out under a total pressure of 80 bars and with potassium iodide instead of the methyltriphenylphosphonium iodide.

(NB): the previous column indicates the number of grams of acetic acid determined.

In Example 12, 20 mmols of sodium acetate were also introduced [$X_T/(A^+ + n.A'^{n+}) = 0.43$].

EXAMPLES 13 TO 21 CONTROL EXPERIMENTS (d) AND (e)

Table II below summarizes the particular conditions and the results obtained in a series of experiments, which had the following conditions in common:

Dicobalt octacarbonyl was employed as the source of cobalt and, unless otherwise indicated, methyltriphenylphosphonium iodide was used (ionic iodide) and a cylindrical plug Z8-CNDT 17-12 steel wire (Afnor Standard Specification), containing 69% of iron, 17% of chromium, 11.5% of nickel, 2% of molybdenum and 0.32% of titanium (the percentages are by weight) and having a specific weight of 525 g/dm³ and an exchange surface of 215 dm²/dm³, was used as the source of iron in the zero oxidation state.

T=210° C., except in Example 21, which was carried out at 180° C.

TABLE II

| Example No. | AcOMe (ml) | AcOH (ml) | Additive nature | Additive ml | Co mg atom/l | I⁻/Co | Plug (g) | P(CO) | P(H₂) | P(T) | t mins. | Ac₂O g | Ac₂O Pr |
|---|---|---|---|---|---|---|---|---|---|---|---|---|---|
| d | 35 | 10 | none | 0 | 20 | 15 | 0 | 130 | 10 | 250 | 36 | 1.58 | 55 |
| 13 | " | " | " | " | " | " | 32.5 | " | " | " | 20 | 5.85 | 350 |
| e | 25 | 5 | NMP | 15 | " | " | 0 | " | " | " | 35 | 6.52 | 220 |
| 14 | " | " | " | " | " | " | 16 | 139 | ≃1.4 | " | 20 | 9.12 | 545 |
| 15 | " | " | " | " | " | " | = 30 to 35 | " | " | " | " | 10.02 | 600 |
| 16 | " | " | " | " | 40 | 7.5 | " | " | " | " | " | 10.24 | 615 |
| 17 | " | " | " | " | 10 | 30 | " | " | " | " | " | 10.49 | 630 |
| 18 | " | " | " | " | 20 | 15 | " | 77 | ≃0.8 | 150 | 30 | 8.19 | 325 |
| 19 | " | " | " | " | " | " | " | 36 | ≃0.5 | 80 | " | 4.61 | 185 |
| 20 | " | " | " | " | " | " | " | 130 | 10 | 250 | 20 | 6.20 | 370 |
| 21 | 30 | 10 | H₂O | 5 | " | " | " | 139 | ≃1.4 | " | " | 21.1 | (xx) | unless otherwise indicated.

TABLE I

| Example No. | AcOMe (ml) | AcOH (ml) | Additive nature | Additive ml | Fe mg atom | P(CO) | P(H₂) | t mins | Ac₂O g | Ac₂O Pr |
|---|---|---|---|---|---|---|---|---|---|---|
| a | 25 | 5 | NMP | 15 | 0 | 130 | 10 | 35 | 6.49 | 220 |
| 1 | " | " | " | " | 89 | " | " | 20 | 13.70 | 820 |
| b | " | " | " | " | " | " | " | 30 | 0.22 | 10 |
| 2 | " | " | " | " | " | 139 | ≃1.4 | 20 | 13.16 | 790 |
| 3 | " | 0 | " | " | " | 130 | 10 | " | 13.31 | 800 |
| 4 | 40 | 5 | none | 0 | 54 | " | " | 30 | 10.15 | 405 |
| c | 40 | " | " | 0 | " | 130 | " | " | 7.18 | 290 |
| 5 | 25 | " | TMS | 15 | " | 139 | ≃1.4 | " | 11.95 | 480 |
| 6 | " | " | " | " | " | 140 | 0 | " | 12.24 | 490 |
| 7 | 30 | 0 | " | " | " | 140 | 0 | " | 12.34 | 495 |
| 8 | 25 | 5 | NMP | 15 | 18 | 130 | 10 | " | 6.16 | 250 |
| 9 | " | " | " | " | 30 | 84 | 6 | 60 | 15.3 | 300 |
| 10 | " | " | " | " | 89 | 36 | ≃0.5 | 30 | 3.57 | 140 |
| 11 | 35 | 5 | H₂O | 5 | 54 | 130 | 10 | " | 15.68 | (NB) |
| 12 | 25 | 5 | NMP | 15 | 53 | 139 | ≃1.4 | " | 9.82 | 390 |

(b): this experiment was carried out in the absence of cobalt.

(c): in this experiment, 3.8 mmols of methyl iodide were also introduced [$X_T(A^+ + n.A'^{n+}) = 1.25$].

In Example 20, the ionic iodide used was KI. (xx): The previous column indicates the number of grams of acetic acid determined.

EXAMPLES 22 TO 29

Table III below summarizes the particular conditions and the results obtained in a series of experiments, which had the following conditions in common:

The reaction was carried out in the presence of 1 mg atom of cobalt (20 mg atom/l) employed in the form of dicobalt octacarbonyl, 15 mmols of methyltriphenylphosphonium iodide ($I^-/Co=15$) and, as the source of iron in the zero oxidation state, a cylindrical plug of Z8 CNDT 17-12 steel described above.

T=212° C.; P(T)=150 bars; P(CO)=77; $P(H_2)=1$; t=2 hours.

TABLE III

| Example No. | AcOMe ml | AcOH ml | Additive nature | Additive ml | Plug (g) | $Ac_2O$ (g) | $Ac_2O$ RY |
|---|---|---|---|---|---|---|---|
| 22 | 40 | 5 | — | 0 | 35.3 | 5.51 | 10.9 |
| 23 | 25 | " | TMS | 15 | 35.2 | 7.65 | 24 |
| 24 | " | " | NMP | " | 35 | 11.73 | 36.7 |
| 25 | " | " | TMU | " | 34.9 | 4.90 | 15.1 |
| 26 | 30 | 0 | NMP | " | 31.3 | 4.33 | 11.3 |
| 27 | " | " | TMS | " | 36.5 | 4.89 | 12.8 |
| 28 | 25 | 5 | NMP | " | 37.9 | 7.85 | 24.6 |
| 29 | 30 | 0 | NMP | " | 34.6 | 3.37 | 8.8 |

EXAMPLES 30 TO 32

A series of experiments was carried out, following the procedure described above, on a reaction charge containing:
(i) 40 ml of AcOMe
(ii) 5 ml of AcOH
(iii) Dicobalt octacarbonyl
(iv) Iron powder
(v) Methyltriphenylphosphonium iodide (Examples 30 and 32) or Tetraethylammonium iodide (Example 31).

The common reaction conditions were as follows:
P(CO)=139
$P(H_2)=1.4$
T=212° C.
P(T)=250 bars
t=30 minutes The particular conditions and also the results obtained are reported in Table IV below:

TABLE IV

| Example No. | Co mg atom | Fe mg atom | Fe/Co | $A + I^-$ mmol | $I^-/Co$ | $Ac_2O$ g | $Ac_2O$ g/h × 1 |
|---|---|---|---|---|---|---|---|
| 30 | 2 | 25 | 12.5 | 10 | 5 | 6.14 | 245 |
| 31 | 1 | 53 | 53 | 20 | 20 | 7.12 | 285 |
| 32 | 0.5 | 100 | 200 | 25 | 50 | 15.79 | 630 |

EXAMPLE 33 CONTROL EXPERIMENT (f)

Using a tantalum autoclave and following the procedure described above, two experiments were carried out on a reaction charge containing:
(i) 30 ml of AcOMe
(ii) 20 ml of NMP
(iii) 1.5 mg atom of cobalt used in the form of dicobalt octacarbonyl
(iv) 30 mmols of lithium iodide.

In Example 33, the charge also contained 54 mg atom or iron powder.

The common conditions were as follows:
P(CO)=32 bars
$P(H_2)=0$
T=152° C.
P(T)=50

The absorption of carbon monoxide was recorded for each experiment. In control experiment (f), it was found that there was no further absorption after a reaction time of 45 minutes at the reaction temperature, but the experiment was nevertheless continued. In Example 33, it was found that the absorption did not stop throughout the duration of the experiment at the reaction temperature.

The particular conditions and also the results obtained are reported in Table V below.

TABLE V

| Reference | Example 33 | Control (f) |
|---|---|---|
| Iron (mg atom) | 54 | 0 |
| t (minutes) | 364 | 256 |
| $Ac_2O$ (g) | 20.71 | 7.95 |
| Absorption time (minutes) | >364 | 45 |

EXAMPLES 34 TO 44

In these examples, the procedure was as follows:

The following materials were introduced into a 300 $cm^3$ stainless steel autoclave which was fitted with a magnetically driven central stirrer and was heated and regulated electrically:
(i) 83 ml of Methyl acetate
(ii) 17 ml of Acetic acid
(iii) 50 ml of N-methylpyrrolidone
(iv) 50 mmols of Methyltriphenylphosphonium iodide
(v) 35 g of a plug of Z8 CNDT 17-12 stainless steel described above
(vi) Dicobalt octacarbonyl The autoclave was heated to the temperature T while sweeping the reactor with carbon monoxide and, if appropriate, hydrogen. The pressure in the autoclave was maintained at 235 bars and the feed rate of the gaseous mixture was 40 l/hour (NTP conditions). The molar percentage of hydrogen in this feed was maintained constant and is indicated in Table VI below.

The reaction mass was sampled periodically and analyzed.

From these analyses, the value of k (rate constant) was determined graphically for each example, the values of log (RY) being plotted on the ordinate and the reaction time (t) at the reaction temperature being plotted on the abscissa. The slope of the experimental line log (RY)=f(t) was equal to the rate constant k, expressed in $hour^{-1}$ ($h^{-1}$).

Table VI below summarizes the particular conditions and also the respective values of k for each example.

TABLE VI

| Example No. | % $H_2$ | T °C. | Co mg atom/l | $I^-/Co$ | k ($h^{-1}$) |
|---|---|---|---|---|---|
| 34 | 0 | 200 | 11.1 | 30 | 0.19 |
| 35 | 0.5 | " | " | " | 0.30 |
| 36 | 1.2 | " | " | " | 0.49 |
| 37 | 2.6 | " | " | " | 0.60 |
| 38 | 4.3 | " | " | " | 0.63 |
| 39 | 10.3 | " | " | " | 0.80 |
| 40 | 4.3 | 180 | " | " | 0.35 |
| 41 | 10.3 | " | " | " | " |
| 42 | " | 200 | 33.5 | 10 | 0.78 |
| 43 | " | " | 5.5 | 60 | 0.65 |

TABLE VI-continued

| Example No. | % H$_2$ | T °C. | Co mg atom/l | I$^-$/Co | k (h$^{-1}$) |
|---|---|---|---|---|---|
| 44 | " | " | 2.8 | 120 | 0.53 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the carbonylation of methyl acetate to produce acetic ahydride in homogeneous liquid phase, the improvement which comprises conducting such carbonylation at a temperature from 80° to 240° C. and under a total pressure from 20 to 300 bars in a virtually anhydrous medium in the presence of:
   (a) a cobalt source;
   (b) a source of iron in the zero oxidation state;
   (c) an ionic iodide of the formula:

$$A^+I^-$$

in which $A^+$ is a nitrogen group quaternary onium cation or an alkali metal cation, the molar ratio $I^-$/Co being greater than or equal to 10; with the total amount of halogen compounds present in the reaction medium, expressed in gram atoms of halogen and designated as $X_T$, being such that the atomic ratio $X_T/(A^+)$ is less than or equal to 1.

2. In a process for the carbonylation of methyl acetate to produce acetic anhydride in homogeneous liquid phase, the improvement which comprises conducting such carbonylation at a temperature from 80° to 240° C. and under a total pressure from 20 to 300 bars in a virtually anhydrous medium in the presence of:
   (a) a cobalt source;
   (b) a source of iron in the zero oxidation state;
   (c) an ionic iodide of the formulae:

$$A^+I^-$$

in which $A^+$ is a nitrogen group quaternary onium cation or an alkali metal cation, the molar ratio $I^-$/Co being greater than or equal to 10; and
   (d) a carboxylate of the formula:

$$A'^{n+}(OCOR)_n{}^-$$

in which n is 1 or 2, $A'^{n+}$ is defined as was $A^+$, with $A'^{n+}$ and $A^+$ being the same or different, and further wherein $A'^{n+}$ may also be an alkaline earth metal cation, and R is an alkyl, aralykl or aryl radical having a maximum of 8 carbon atoms; with the total amount of halogen compounds present in the reaction medium, expressed in gram atoms of halogen and designated by $X_T$, being such that the atomic ratio $X_T/(A^+ + n.A'^{n+})$ is less than or equal to 1.

3. The process as defined by claims 1 or 2, wherein the source of iron in the zero oxidation state is iron metal, Fe(CO)$_5$ or iron alloys, the content in iron of which being at least 20% by weight.

4. The process as defined by claim 3, said source of iron in the zero oxidation state being iron metal.

5. The process as defined by claim 3, said source of iron in the zero oxidation state being an alloy of iron, the content in iron of which being at least 20% by weight.

6. The process as defined by claims 1 or 2, said carbonylation also being carried out in the presence of hydrogen.

7. The process as defined by claim 6, wherein the hydrogen partial pressure, measured at 25° C., is at least 1 bar.

8. The process as defined by claims 1 or 2, wherein the carbon monoxide partial pressure, measured at 25° C., is at least 10 bars.

9. The process as defined by claims 1 or 2, wherein the cobalt concentration ranges from 0.1 to 500 mg atoms/l.

10. The process as defined by claim 7 wherein the hydrogen partial pressure, measured at 25° C., is less than 100 bars.

11. The process as defined by claim 9, wherein the molar ratio $I^-$/Co ranges from 15 to 100.

12. The process as defined by claim 9, wherein the atomic ratio Fe/Co is at least 1.

13. The process as defined by claim 12, wherein the atomic ratio Fe/Co is at least 10.

14. The process as defined by claim 12, wherein the ionic iodide is a quaternary phosponium or quaternary ammonium iodide.

15. The process as defined by claim 12, wherein the ionic iodide is an alkali metal iodide.

16. The process as defined by claim 2, wherein the molar ratio $A'^{n+}/A^+$ ranges from 0.01 to 20.

17. The process as defined by claim 12, wherein the reaction is carried out at a temperature below 160° C., under a total pressure, at such temperature, of less than 100 bars, and in a tetramethylenesulfone, tetramethylurea, N-methylpyrrolidone or monocarboxylic acid amide solvent, such amide solvent being derived from an acid having a maximum of 8 carbon atoms, and in which the nitrogen atom contains two alkyl substituents having a maximum of 4 carbon atoms.

18. The process as defined by claims 1 or 2, wherein the reaction is carried out at a temperature which is above or equal to 160° C. and under a total pressure, at such temperature, which is greater than or equal to 100 bars.

19. The process as defined by claim 20, wherein the reaction medium comprises an aliphatic carboxylic acid solvent having a maximum of 8 carbon atoms.

20. The process as defined by claim 19, said solvent being acetic acid.

* * * * *